United States Patent [19]
Myers et al.

[11] Patent Number: 5,466,217
[45] Date of Patent: * Nov. 14, 1995

[54] IONTOPHORETIC DRUG DELIVERY APPARATUS

[75] Inventors: Robert M. Myers, Stanford; Ronald P. Haak, San Jose; Richard W. Plue, San Francisco, all of Calif.

[73] Assignee: Alza Corporation, Palo Alto, Calif.

[*] Notice: The portion of the term of this patent subsequent to May 17, 2011, has been disclaimed.

[21] Appl. No.: 222,122

[22] Filed: Apr. 4, 1994

Related U.S. Application Data

[63] Continuation of Ser. No. 889,950, Jun. 2, 1992, Pat. No. 5,312,326.

[51] Int. Cl.⁶ .................................................. A61N 1/30
[52] U.S. Cl. ........................................... 604/20; 607/152
[58] Field of Search ............................... 604/20; 128/798, 128/802, 803

[56] References Cited

U.S. PATENT DOCUMENTS

| | | |
|---|---|---|
| 3,989,816 | 11/1976 | Rajadhyaksha . |
| 3,991,755 | 11/1976 | Vernon et al. . |
| 4,141,359 | 2/1979 | Jacobsen et al. . |
| 4,250,878 | 2/1981 | Jacobsen et al. . |
| 4,383,529 | 5/1983 | Webster . |
| 4,398,545 | 8/1983 | Wilson . |
| 4,405,616 | 9/1983 | Rajadhyaksha . |
| 4,415,563 | 11/1983 | Rajadhyaksha . |
| 4,424,210 | 1/1984 | Rajadhyaksha . |
| 4,474,570 | 10/1984 | Ariura et al. . |
| 4,622,031 | 11/1986 | Sibalis . |
| 4,708,716 | 11/1987 | Sibalis . |
| 4,722,726 | 2/1988 | Sanderson et al. . |
| 4,725,263 | 2/1988 | McNichols et al. . |
| 4,865,582 | 9/1989 | Sibalis . |
| 4,883,457 | 11/1989 | Sibalis . |
| 4,927,408 | 5/1990 | Haak et al. . |
| 4,942,883 | 7/1990 | Newman . |
| 5,023,085 | 6/1991 | Francoeur et al. . |
| 5,160,316 | 11/1992 | Henley . |
| 5,167,167 | 12/1992 | Sibalis . |
| 5,312,326 | 5/1994 | Myers et al. .................... 604/20 |

FOREIGN PATENT DOCUMENTS

| | | |
|---|---|---|
| 0092015 | 10/1983 | European Pat. Off. . |
| 0513879 | 11/1992 | European Pat. Off. . |
| 1802 | 5/1914 | Netherlands . |
| 410009 | 5/1934 | United Kingdom . |
| WO90/06153 | 6/1990 | WIPO . |
| WO93/09842 | 5/1993 | WIPO . |

*Primary Examiner*—C. Fred Rosenbaum
*Assistant Examiner*—Frank Wilkens, III
*Attorney, Agent, or Firm*—Grady J. Frenchick; Stroud, Stroud, Willink, Thompson & Howard

[57] ABSTRACT

An iontophoretic agent delivery device having a simplified structure and ease of manufacture. The device utilizes an electrical pathway comprising a source of electrical energy and an output means. The electrical pathway is disposed upon one of the two sides of a flexible, non-conductive substrate (e.g., a film). The output means of the pathway are connected directly or indirectly, e.g., by means of an electrically conductive adhesive tape, to the remaining components of the device such as current distribution members, lead wires, or electrodes. In this arrangement, the circuit is inverted from that of conventional devices. Economical, reel-to-reel methods of manufacturing a one-sided iontophoretic circuit apparatus of the invention are disclosed.

2 Claims, 2 Drawing Sheets

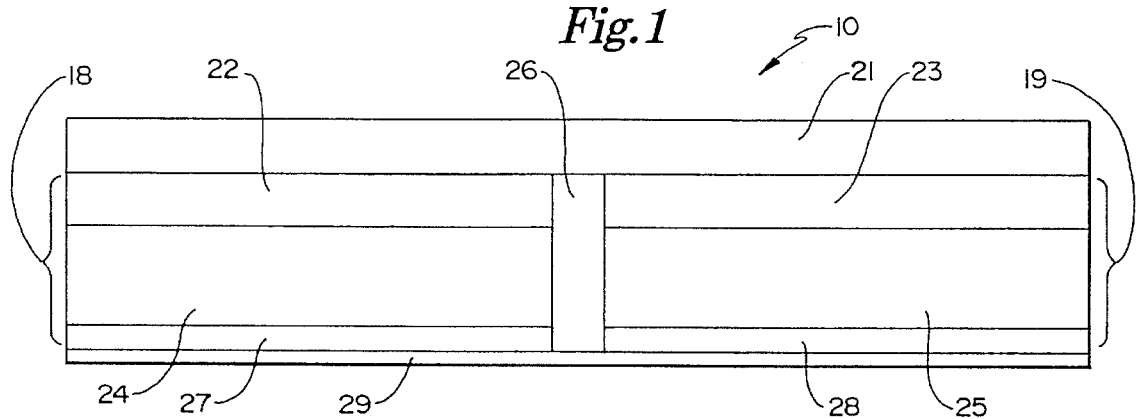
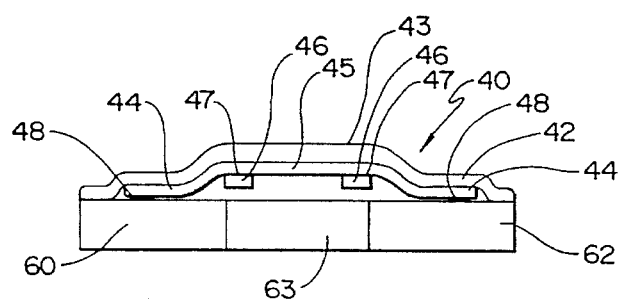
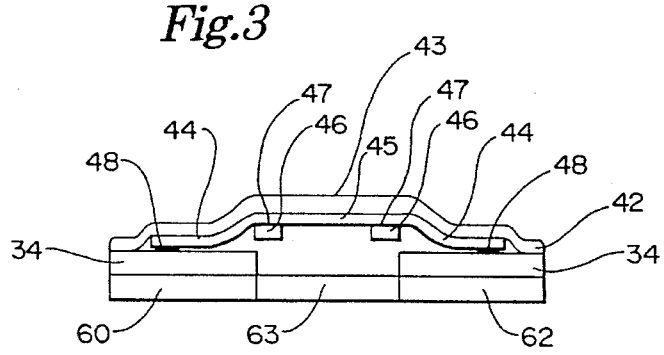

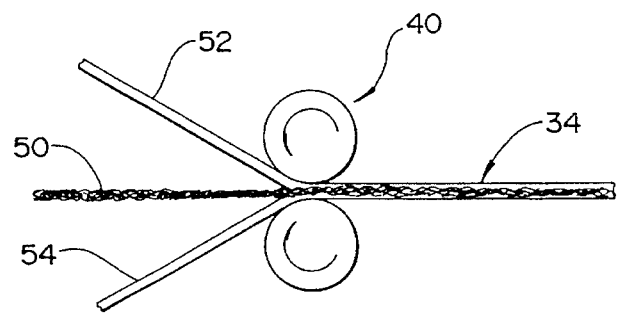
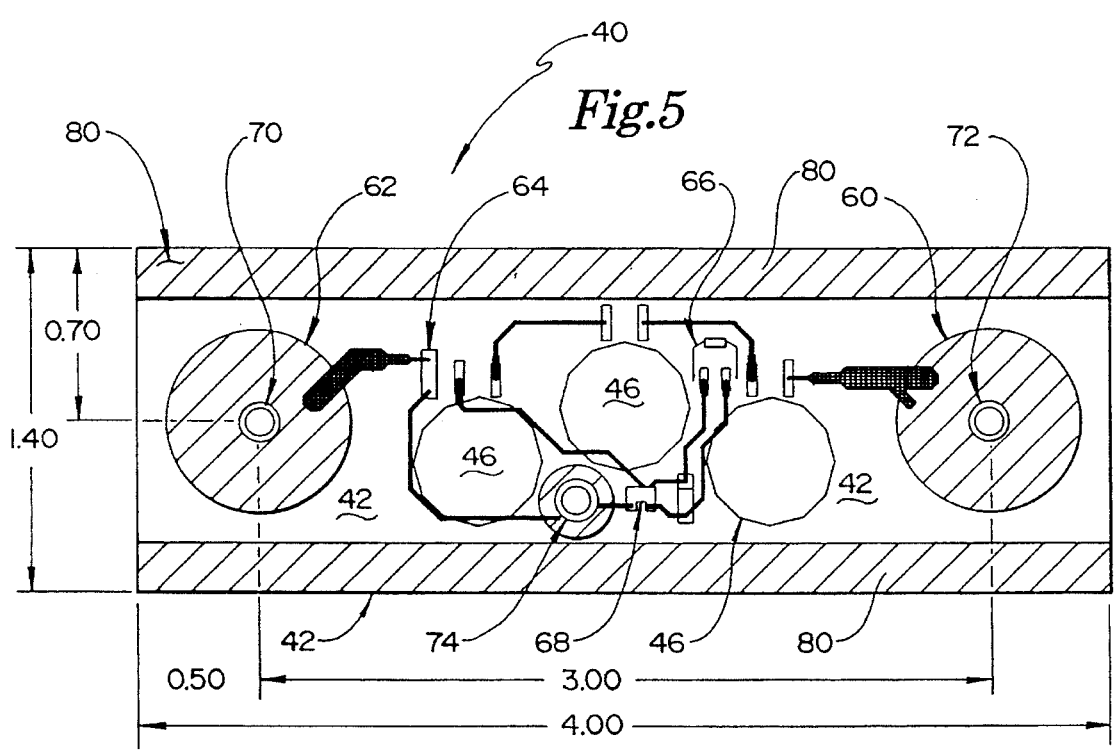

IONTOPHORETIC DRUG DELIVERY APPARATUS

This is a continuation of application Ser. No. 07/889,950 filed Jun. 2, 1992, now U.S. Pat. No. 5,312,326.

Reference is made to concurrently filed, commonly owned patent application Ser. No. 07/889,950 now U.S. Pat. No. 5,312,326, entitled "IONTOPHORETIC DRUG DELIVERY APPARATUS". The teaching of this concurrently filed patent application is incorporated by reference herein.

TECHNICAL FIELD

The present invention generally concerns apparatuses, systems, applicators, or devices for the electrically assisted administration or delivery of therapeutic agents or species. This invention also concerns methods for making such apparatuses.

More specifically, this invention concerns low cost, generally disposable, electrically-assisted drug or therapeutic agent delivery systems. Yet more specifically, this invention relates to apparatuses for iontophoretic drug delivery in which, preferably flexible circuits are electrically connected or coupled to other, separate components or sub-assemblies of the apparatus in an inexpensive yet rapidly manufacturable manner. Lastly, this invention relates to disposable iontophoretic drug delivery systems.

BACKGROUND OF THE INVENTION

The present invention concerns apparatuses and methods for transdermal delivery or transport of therapeutic agents, typically through iontophoresis. Herein the terms "iontophoresis" and "iontophoretic" are used to refer to methods and apparatus for transdermal delivery of therapeutic agents, whether charged or uncharged, by means of an applied electromotive force to an agent-containing reservoir. The particular therapeutic agent to be delivered may be completely charged (i.e., 100% ionized), completely uncharged, or partly charged and partly uncharged. The therapeutic agent or species may be delivered by electromigration, electroosmosis or a combination of the two. Electroosmosis has also been referred to as electrohydrokinesis, electroconvection, and electrically-induced osmosis. In general, electroosmosis of a therapeutic species into a tissue results from the migration of solvent, in which the species is contained, as a result of the application of electromotive force to the therapeutic species reservoir.

As used herein, the terms "iontophoresis" and "iontophoretic" refer to (1) the delivery of charged drugs or agents by electromigration, (2) the delivery of uncharged drugs or agents by the process of electroosmosis, (3) the delivery of charged drugs or agents by the combined processes of electromigration and electroosmosis, and/or (4) the delivery of a mixture of charged and uncharged drugs or agents by the combined processes of electromigration and electroosmosis.

Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current. That current requirement meant that the patient needed to be immobilized near the current source. The device of that British specification was made by forming a galvanic cell from the electrodes and the material containing the medicament or drug to be transdermally delivered. The galvanic cell produced the current necessary for iontophoretically delivering the medicament. This portable device thus permitted iontophoretic drug delivery with substantially less interference with the patient's daily activities.

More recently, a number of United States patents have issued in the iontophoresis field, indicating a renewed interest in this mode of drug delivery. For example, Vernon et al. U.S. Pat. No. 3,991,755; Jacobsen et al. U.S. Pat. No. 4,141,359; Wilson U.S. Pat. No. 4,398,545; and Jacobsen U.S. Pat. No. 4,250,878 disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate and many other drugs. Perhaps the most common use of iontophoresis is in diagnosing cystic fibrosis by delivering pilocarpine. Iontophoretically delivered pilocarpine stimulates sweat production, the sweat is collected, and is analyzed for its chloride ion content. Chloride ion concentration in excess of certain limits suggests the possible presence of the disease.

In presently known iontophoresis devices, at least two electrodes are used. Both of these electrodes are disposed so as to be in intimate electrical contact with some portion of the skin of the body. One electrode, called the active or donor electrode, is the electrode from which the ionic substance, agent, medicament, drug precursor or drug is delivered into the body via the skin by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be driven into the body is positively charged, then the anode will be the active electrode and the cathode will serve to complete the circuit. If the ionic substance to be delivered is relatively negatively charged, then the cathodic electrode will be the active electrode and the anodic electrode will be the counter electrode.

Alternatively, both the anode and the cathode may be used to deliver drugs of appropriate charge into the body. In such a case, both electrodes are considered to be active or donor electrodes. For example, the anodic electrode can drive positively charged substances into the body while the cathodic electrode can drive negatively charged substances into the body.

Furthermore, existing iontophoresis devices generally require a reservoir or source of the ionized or ionizable species (or a precursor of such species) which is to be iontophoretically delivered or introduced into the body. Examples of such reservoirs or sources of ionized or ionizable species include a pouch as described in the previously mentioned Jacobsen U.S. Pat. No. 4,250,878, a pre-formed gel body as disclosed in Webster U.S. Pat. No. 4,382,529 and a generally conical or domed molding of Sanderson et al., U.S. Pat. No. 4,722,726. Such drug reservoirs are electrically connected to the anode or to the cathode of an iontophoresis device to provide a fixed or renewable source of one or more desired species or agents.

Recently, the transdermal delivery of peptides and proteins, including genetically engineered proteins, by iontophoresis, has received increasing attention. Generally speaking, peptides and proteins being considered for transdermal or transmucosal delivery have a molecular weight in the range of greater than about 500 Daltons to a molecular weight of 40,000 Daltons (or more). These high molecular weight substances are usually too large to diffuse passively (i.e., without electromotive force) through skin at therapeutically effective rates. Since many peptides and proteins carry either a net positive or net negative charge and because of their inability to diffuse passively through skin at therapeutically useful rates, they are considered likely candidates for iontophoretic delivery as defined herein.

Several approaches have been used to couple or to connect components of an iontophoresis apparatus such as the circuitry to the electrodes. One approach has been to employ a two-sided circuit board. A two-sided circuit board uses connective, conductive conduits or "through holes" to connect the two circuits through the non-conductive circuit substrate or circuit board. The output terminals of the underside circuit then would be in physical and electrical contact with the remaining components of the device. Producing a two-sided circuit board with connective conduits is relatively costly.

Another approach has been to use a single-sided circuit assembly or board and folding the output terminals under the main part of the circuit to create a device configuration that is a flattened circle (with a segment of the circle at its bottom missing) in section. Again this permits physical contact between the circuit output terminals and the rest of the device, (e.g., the electrodes). This approach tends to produce stress points at the folds which can cause the circuit to separate.

Electrotransport devices having elaborate circuitry have also been suggested in the art. Such devices, to date, have been thought of as too costly for utilization in a disposable electrotransport device.

From a commercial standpoint, it is generally desirable for an iontophoresis apparatus to be manufacturable in a cost effective manner, preferably in large quantities. This invention provides apparatuses and methods of manufacture capable of achieving both objectives.

DISCLOSURE OF THE INVENTION

Briefly, in one aspect, the present invention is an iontophoresis apparatus, applicator, or assembly, comprising a single-sided, preferably flexible, electrical circuit. The single-sided electrical circuit is coupled to a source of electrical energy, such as a battery, and further is coupled or connected to further components of the apparatus such as electrodes as described above. "Coupled," as the term is used herein, means connected physically or electrically, directly or indirectly, i.e., through further components or connector means. A flexible circuit of this invention comprises a relatively non-conducting flexible member or substrate having opposing first and second surfaces. An example of such a member is a segment of flexible film. The member has at least one conductive (or at least controllably conductive) electronic circuit or pathway printed, deposited, or adhered on one side or one of the opposing surfaces thereof. At least a portion of the electrical circuit is juxtaposed against, and preferably is in direct electrical and physical contact with the rest of the apparatus structure, e.g., the electrodes. For example, the output terminals of the circuit could be in direct physical and electrical contact with the electrodes. This arrangement requires the electrical circuit to be on the same side of the member as the electrodes or other components of the electrotransport apparatus to which the circuitry is coupled. In a preferred embodiment, the other or remaining surface or side of the flexible member is juxtaposed against or is overlain by a flexible, protective non-adhesive film cover, backing, or protective layer.

Thus, in a preferred embodiment, the arrangement of components of an apparatus of this invention from its top (or outside) to its bottom (or skin-side) is optional protective film, flexible member —first opposing surface, flexible member—second opposing surface, electronic pathway (the member and electronic pathway comprise a one-sided circuit) and the rest of the iontophoresis apparatus structure such as electrodes means, e.g., electrodes. Generally speaking, a source of electrical energy will be coupled to the electronic pathway (e.g., a battery output terminal will be connected to a circuit input terminal) and be located on the same side of the flexible member. In order for the various layers to adhere to each other, suitable adhesives can be disposed therebetween. Alternatively, thermoplastic materials or layers can be sealed to each other, e.g., with heat.

Describing the above invention in another manner, the apparatus comprises an iontophoretic medicament or agent delivery apparatus comprising a one-sided or single-sided circuit means having a top or exterior side and a bottom or interior side. The frame of reference of the previous sentence is that the first, top, or upper side of the single-sided circuit would be the exterior side or the side furthest away from the site at which drug is to be iontophoretically delivered. The second, bottom, or underside then would be the interior side of the one-sided circuit or the side of the circuit closest to the site to which drug is to be iontophoretically delivered. In either instance, in this embodiment, the conductive, flexible electronic pathway (which would include input means and output means) would be disposed on the second or bottom side of the member. In a preferred practice, the member comprises a segment of film which optionally may include a plurality of sprocket holes located along one or both sides thereof, similar to the base substrate for 35 mm photographic film. In common terms, the electronic pathway of the present invention including input means, signal treatment segment and output means, are "upside down" or inverted with its top toward the patient. Completing the apparatus, the circuit means input would be coupled to a source of electrical energy such as a battery. In order to obtain the least complex structure, electrical energy sources, such as batteries will generally be located on the same side of the non-conductive member or substrate as the electronic pathway. The electronic circuit output means then would be coupled to the rest of the iontophoretic drug delivery apparatus structure, generically referred to as electrode means. This would mean, for example, the electronic circuit output means could be coupled to electrode current distribution members or other electrode structures. This means, for example, that the electronic circuit output means or pads could be in direct physical and electrical contact with, e.g., a current distribution member, of an electrode.

In another construction of the present invention, the one-sided, upside-down circuit can be coupled to the rest of the apparatus by means of an electronically conductive adhesive tape means such as that described in the concurrently-filed co-pending and co-owned U.S. patent application, Ser. No. 07/889,950, said application being entirely incorporated by reference herein. An electrically conductive adhesive means such as, for example, an electrically conductive adhesive tape, would permit there to be a significant physical separation between circuit output means and, e.g., electrode means. In its broadest application, the present invention permits simplification of iontophoretic apparatus structure by providing direct physical contact (or indirect coupled contact) between circuit output and electrode means input.

"Flexible" as the term is used herein, means being capable of conforming to the contours of a portion of the body to which the device is attached or to which it most closely approaches, i.e., to be conformable to a highly contoured body surface such as an arm, a leg, or the chest. "Flexible", as used herein, also means being capable of bending, twisting, or deforming so as to continue to conform to the contours of the area of the body to which the device is attached throughout the normal range of movement of the body area. For an entire device to be "flexible", as defined herein, generally speaking, each of its components also must be flexible.

"Conductive" as the term is used herein means having a bulk electronic conductivity of greater than about 1 ohm cm.

"One-sided" or "single-sided" circuit or circuitry as those terms are used herein means lying or being disposed upon substantially a single side of a support substrate, member, or film. In its preferred usage, this definition requires that the circuit elements of a device to which it applies would be substantially co-planar.

BRIEF DESCRIPTION OF THE DRAWINGS

A better understanding of the present invention as well as other objects and advantages thereof will become apparent upon consideration of the following detailed description especially when taken with the accompanying drawings, wherein like numerals designate like parts throughout, and wherein:

FIG. 1 is a side sectional view showing the primary components of an iontophoretic delivery device as described above;

FIG. 2 is a side, sectional view of an apparatus of the invention;

FIG. 3 is a sectional view of a second embodiment of the present invention;

FIG. 4 is a sectional view of a preferred electronically conductive adhesive material useable in this invention; and FIG. 5 is a an overhead view of a constant current circuit useable in the present invention.

Modes of Carrying Out the Invention

Thus, FIG. 1 is a side sectional depiction of an iontophoretic delivery device 10. It is to be understood that apparatus 10 can have essentially any convenient size or shape, whether square, oval, circular, or tailored for a specific location on the skin. As depicted, device 10 would generally be applied to the skin of a patient by means of a suitable bio-compatible adhesive material. Device 10 is preferably flexible as defined herein. Device 10 has a top layer 21 which contains a source of electrical energy (e.g., a battery or a series of batteries) as well as optional control circuitry for current regulation e.g., a resistor or a transistor-based current control circuit, an on/off switch, and/or a microprocessor adapted to control the current output of the power source over time. Layer 21 generally contains all components necessary to deliver current of predeterminable characteristics to the rest of the components of the device. Layer 21 is "flexible" as defined above, and generally is comprised of an electronic circuit disposed upon a thin, flexible substrate or support such as, for example, a film or polymeric web as will be described in greater detail below.

Device 10 further comprises electrode means or assemblies indicated by brackets 18 and 19. Electrode assemblies 18, 19 may contain further electrode structure such as current distribution members to eliminate "hot spots". Electrodes assemblies 18 and 19 are separated from one another by an electrical insulator 26, and form therewith a single, self-contained unit. For purposes of illustration, the electrode assembly 18 is sometimes referred to as the "donor" electrode assembly while electrode assembly 19 is sometimes referred to as the "counter" electrode assembly. These designations of the electrode assemblies are not critical and may be reversed in any particular device or in operation of the device shown.

In the embodiment of FIG. 1, a donor electrode 22 is positioned adjacent a drug reservoir 24 while a counter electrode 23 is positioned adjacent a reservoir 25 which contains an electrolyte. Electrodes 22 and 23 may comprise metal foils, or a polymer matrix loaded with metal powder, powdered graphite, carbon fibers, or any other suitable electrically conductive material. Reservoirs 24 and 25 can be polymeric matrices or gel matrices. Natural or synthetic polymer matrices may be employed. Insulator 26 is composed of an electrically insulating and non-ion-conducting material which acts as a barrier to prevent short-circuiting of the device 10. Insulator 26 can be an air gap, a non-ion-conducting and electrically insulating polymer or adhesive, or other suitable barrier to ion and charge flow. The device 10 optionally can be adhered to the skin by means of ion-conducting adhesive layers 27 and 28. The device 10 also optionally includes a strippable release liner 29 which is removed just prior to application of the device to the skin. Alternatively, device 10 can be adhered to the skin by means of an adhesive overlay of the type which are conventionally used in transdermal drug delivery devices. Generally speaking, an adhesive overlay would contact the skin around the perimeter of the device to maintain contact between reservoirs 24 and 25 and the patient's skin. Thus, for purposes of orientation, the "top" exterior, or outside, of device 10. would be closest to the top of FIG. 1. Conversely, the bottom, interior or inside of the device would be in the direction of the bottom of FIG. 1.

In a typical device 10, the drug reservoir 24 contains an ionized, or ionizable supply of the drug or agent to be delivered and the counter reservoir 25 contains a suitable electrolyte such as, for example, sodium chloride, sodium phosphate, or mixtures thereof. Alternatively, device 10 can contain an ionizable, or neutral supply of drug in both reservoirs 24 and 25 and in that manner both electrode assemblies 18 and 19 would function as donor electrode assemblies. For example, positive drug ions could be delivered through the skin from the anode electrode assembly, while negative drug ions could be delivered from the cathode electrode assembly. Generally, the combined skin-contacting area of electrode assemblies 18 and 19 can range from about 1 cm$^2$ to about 200 cm$^2$, but typically will range from about 5 cm$^2$ to about 50 cm$^2$.

In accordance with the present invention, the drug reservoir 24 and return reservoir 25 of the iontophoretic delivery device 10 must be placed in agent or drug transmitting relation with the patient so as to iontophoretically deliver agent or drug. Usually this means the device is placed in intimate contact with the patient's skin after removal of any release liner. Various sites on the human body may be selected depending upon the physician's or the patient's preference, the drug or agent delivery regimen, or other factors such as cosmetic.

FIGS. 2 and 3 illustrate, in schematic section, two embodiments of the present invention. FIG. 2 illustrates an embodiment of the present invention wherein the "upside down" or inverted flexible circuit of the invention is placed in direct physical/electrical contact with the rest of the apparatus structure. Flexible, one-sided or single-sided circuit 40 comprises a substantially non-conductive, flexible substrate 42 on which there is disposed a conductive pathway 44. Substrate 42 has opposed first and second surfaces 43, 45, respectively. Pathway 44 is disposed on second surface 45. Batteries 46 are electrically connected to conductive pathway 44 (at interface 47).

Batteries 46, in this embodiment, comprise button cells. Many other sources of electrical energy (including flexible polymeric or sheet batteries) could be utilized without departing from the scope or intent of this invention. Conductive pathway 44 has output means, e.g., output pads, 48. Output pads 48 directly touch and therefore physically and electrically couple to electrode means 60, 62, respectively. Electrically and ionically non-conductive separator 63 is disposed between electrode means 60 and 62. While not critical, electrode means 60 is the anode and electrode means 62 is the cathode. Depending upon preference there may be further layers or layers overlying flexible substrate 42. Also the apparatus may comprise additional structure, e.g., a drug reservoir and an electrolyte reservoir, coupled to electrode means 60, 62, respectively. These further structures have been intentionally omitted so as not to detract from illustration of the invention.

FIG. 3 illustrates an embodiment of the present invention in which an electrically conductive adhesive means 34 is used to electrically connect output pads 48 to electrode means 60, 62, respectively. In this embodiment, electrically conductive adhesive means 34 comprises flexible electrically conductive adhesive tape (ECAT). ECAT 34 can be of simple or complex structure depending upon the particular application, as long as the structure is electrically conductive, adhesive and, preferably, flexible. As shown, ECAT 34 couples circuit output means or pads 48 and electrode means 60, 62. ECAT 34 creates an efficient coupling of the areas which are the circuit output pads and at least the back side of anode 60 and cathode 62, respectively. Other types of coupling means or connectors may be placed between output pads 48 and electrode means 60, 62 without deviating from teaching of the present invention.

Although the ECA of the present invention is not limited to any particular structure or composition, one particularly preferred ECA is formed by laminating one or more layers 52, 54 of an adhesive material to one or more electrically conductive webs, mats or meshes 50 to form a composite ECA 34 as shown in FIG. 4. One particularly useful composite ECA 34 is formed by laminating between opposing laminating rollers 40 a single conductive mat or mesh 50 between two adhesive layers 52, 54. Lamination is conducted at a suitable temperature and pressure to ensure that layers 52 and 54 "flow" into the interstitial spaces between the fibers/strands of mesh 50 and intimately contact and adhere to the fibers/strands of mesh 50 so that the entire composite ECA 34 is flexible, adhesive, conductive and has a substantially uniform cross-section. A composite ECA (not shown) formed by laminating a single adhesive layer 52 to a single conductive mesh 50 is also suitable. An alternative composite ECA 34 (not shown) can be formed by laminating two conductive meshes 50 with a single layer 52 of adhesive sandwiched therebetween.

Mat or mesh 50 may be of any suitable conductive, flexible structure. For example, mat or mesh 50 can have an open weave design which approximates a screen. One preferred mat is made of 100% nylon strands, type 6—6, 40 denier, 13 filaments per end and has a thickness of approximately 0.025 inches. This open-weave material has its interwoven strands coated with an electrically conductive material such as graphite, carbon, silver, silver oxide, aluminum powder, or gold. The mat has a resultant surface resistance of less than 10 ohms per square inch, a tensile strength in excess of 125 pounds per square inch and a tear strength in excess of 10 pounds per square inch. This material may be obtained from Tecknit® Corporation, Cranford, N.J. Other electrically conductive adhesive materials are described in the concurrently filed patent application cross-referenced above.

A particularly preferred composite ECA is formed by laminating at least one layer of an intermingled, non-woven, carbon fiber matting and at least one other layer of an adhesive polyisobutylene matrix. The non-woven carbon fiber matting can have a weight of about 3 to 70 g/m$^2$. The carbon fiber matting comprises about 1 to 10 volume percent, and preferably about 2 to 5 volume percent, of the total volume of the ECA. This ECA is made by laminating the polyisobutylene (PIB) into the carbon fiber mat so that the PIB flows therein and becomes intimately admixed therewith. Within the above limits, various equivalent formulations will become apparent to one of ordinary skill in this art. The preferred composite ECA may be produced by laminating the conductive mesh to one layer, or between two layers, of adhesive matrix. For example, sheet PIB, in rolled form, and kept usable by wrapping it with two release liners, is unrolled and laminated onto one or both major surfaces of a non-woven, conductive carbon mesh. In this manner, an ECA in sheet form, such as that shown in FIG. 4, is produced. The sheet can then be cut or otherwise processed into suitable lengths, shapes or configuration(s) for use in an electrotransport device.

FIG. 5 is an illustration of a specific flexible, one-sided circuit assembly of the present invention. Circuit 40 comprises non-conductive flexible substrate 42 and a series of components which comprise the electrical pathway generally designated 44 in FIGS. 2 and 3. Substrate 42 is preferably a segment of flexible film, similar to the film base used in 35 mm photographic film. Circuit 40 is a constant current device useable in an iontophoretic drug delivery apparatus where variable load resistances and supply voltages occur. Circuit 40 comprises output pads 48a and 48b. Output pad 48a is adapted to be electrically connected (either directly as shown in FIG. 2 or indirectly through ECAT layer 34 as shown in FIG. 3) to anode 60. Similarly, output pad 48b is adapted to be electrically connected to cathode 62. As shown, output pad 48a is electronically coupled to 100 ohm resistor 64, a 0–22 kilo ohm variable resistor 66 and to Field Effect Transistor 68. Three 3-volt button cell lithium batteries 46 complete circuit 40. Continuity test points 70, 72, 74 are indicated on the circuit.

Shown cross-hatched in FIG. 5 is a "keep out" or excluded zone 80. Zone 80 provides a perimeter space in which or on which, for example, sprocket holes 43 or other film transport means could be provided. Sprocket holes would provide the means by which circuits could be rapidly and cheaply processed in a continuous fashion. In this manner low cost, relatively inexpensive flexible circuits could be produced. Typical dimensions of a single-sided or one-sided circuit or backing 42 would be a total film width of approximately 1.4 cm, a circuit repeat distance of approximately 4.0 cm, and "keep out" zone width of approximately 0.2 cm. Sprocket holes 43 can be separated a distance determined by the ease or difficulty of advancing the film substrate during processing. Typically, sprocket holes 43 would be separated a distance of 0.5 cm.

Flexible, relatively thin pathways or circuits can be applied to a flexible film substrate using standard flex circuit processing techniques. For example, printing, depositing, or etching processes can be used to create copper or silver circuit pathways on flexible film substrates. Reel-to-reel processes can be used rapidly to mate the flexible film substrate which carries the electrically conductive circuit to one or more additional substrates (e.g., a backing layer film substrate or a donor and counter electrode film substrate). For example, flexible film substrates with printed, deposited or etched circuits can be received in reel form or rolled form. A polymeric film backing material can also be received in reel or rolled form. After appropriate alignment, the electrical components are then mated with the backing material to create a bi-layer (e.g., backing layer and circuit layer) composite work piece or material in continuous ribbon form in a single, rapidly repeatable step. For example, the circuits can be rolled onto or into the backing material by application of rolling or roller pressure. If necessary, a pressure sensitive adhesive can be used to adhere the circuit layer to the backing layer. The bi-layer composite material is then cut to produce individual units comprised of a flexible circuit layer and a backing layer. After inversion, the individual units are joined to the donor and counter electrode assemblies to form completed iontophoretic devices again, using automated (e.g., pick-and-place) processes. In this manner, automated manufacture and concomitant cost savings can be achieved.

As noted, a source of electrical energy, e.g., one or more batteries, is incorporated into the electrical pathway before or at the time of assembly of the circuit. Batteries also can be included as part of the flexible circuit before it is applied to the substrate. Alternatively batteries can be connected or coupled to the circuit later, e.g., at the time of activation of the device, using known mechanical or electrical contacts. The complete device then can be activated by medical personnel or the patient depending upon the drug or agent delivery protocol.

A battery useable in this invention can be made up of a group of cells internally connected in series to obtain the desired voltage necessary to obtain the electrophoretic action with the particular medicament. The exact orientation of a battery would depend on whether the charged (ionic) particles of the drug of choice are positive or negative. If the particles are negatively charged in solution or suspension then the battery or batteries are oriented so that the negative battery terminal is connected to the donor electrode and the positive battery terminal is connected to the counter electrode. The converse would apply if positively charged species are to be delivered. Any conventional miniaturized battery cells, e.g., button cells, now generally available can be employed, arranged and connected in series to obtain the desired operating voltage.

In addition, the technology now exists for batteries which are made up of very thin, flexible sheets of a conductive polymer with high surface areas relative to thickness to provide adequate current densities. One such so-called plastic battery is described in "Batteries Today", Autumn 1981, pages 10, 11, and 24. When such a battery is employed, sheets may be layered to place the cells in series. Of course, battery selection would ultimately depend on such factors as the degree of flexibility or conformability desired, current density required for a specific application, and time of discharge. Whether miniature batteries or sheet batteries are employed, battery output terminals can be directly or indirectly connected, e.g., by wires, printed circuitry or by electrically conductive adhesive means, to circuit input means or pads.

The terms "agent" or "drug" are used extensively herein. As used herein, the expressions "agent" and "drug" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, anti-depressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, polypeptides and other macromolecules, psychostimulants, sedatives and tranquilizers.

It is believed that an apparatus of the present invention can be used to deliver the following drugs: baclofen, betamethasone, beclomethasone, buspirone, cromolyn sodium, dobutamine, doxazosin, droperidol, fentanyl, sufentanil, ketoprofen, lidocaine, metoclopramide, methotrexate, miconazole, midazolam, nicardipine, prazosin, piroxicam, scopolamine, testosterone, verapamil, tetracaine, diltiazem, indomethacin, hydrocortisone, terbutaline and encainide.

This invention is also believed to be useful in the iontophoretic delivery of peptides, polypeptides and other macromolecules typically having a molecular weight of at least about 300 Daltons, and typically a molecular weight in the range of about 300 to 40,000 Daltons. Specific examples of peptides and proteins in this size range include, without limitation, LHRH, LHRH analogs such as buserelin, gonadorelin, naphrelin and leuprolide, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.,), follicle leutoids, αANF, growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hyaluronidase, interferon, interleukin-2, menotropins (urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 anti-trypsin (recombinant).

Generally speaking, it is most preferable to use a water soluble salt of the drug or agent to be delivered. Drug or agent precursors, i.e., species which generate the selected species by physical or chemical processes such as ionization, dissociation, or dissolution, are within the definition of "agent" or "species" herein. "Drug" or "agent" is to be understood to include charged and uncharged species as described above.

In certain cases, it may be desirable to deliver the drug or agent with one or more skin permeation enhancers. A skin permeation enhancer can be selected from any of a wide variety of known materials capable of enhancing transdermal drug flux. Known permeation enhancers include, for example, surfactants, alkyl substituted sulfoxides, alkyl polyethylene glycols, lower alcohols and the permeation enhancers disclosed in U.S. Pat. Nos. 3,989,816; 4,405,616; 4,415,563; 4,424,210; 4,722,726; and 5,023,085 all of which are incorporated herein by reference.

The above disclosure will suggest many alternatives, permutations, and variations of the invention to one of skill in this art. This disclosure is intended to be illustrative and not exhaustive. All such permutations, variations and alternatives suggested by the above disclosure are to be included within the scope of the attached claims.

What is claimed is:

1. A flexible, electrically-powered iontophoresis apparatus for delivery of an agent through a body surface comprising:

a flexible, non-conductive substrate having opposing major surfaces, one of the major surfaces being oriented to face the body surface, the other surface being oriented to face away from the body surface;

a substantially planar, conductive, electronic pathway disposed on the major surface of the substrate facing the body surface, the electronic pathway including an input means and an output means which are electronically connected, the output means being electrically connected to an electrode means and the input means being electronically connected to a source of electrical energy; whereby electrical and physical connection is achieved between the conductive pathway and the electrode in the absence of conductive pathway stress due to folding of the pathway.

2. An iontophoresis apparatus according to claim 1 which further includes a protective film having an exterior surface and an interior surface, the non-conductive substrate being disposed on the interior surface of the film.

* * * * *